United States Patent
Knipfer

(10) Patent No.: US 10,130,455 B2
(45) Date of Patent: Nov. 20, 2018

(54) EXPANDABLE IMPLANT SYSTEM

(71) Applicant: Boston Scientific Scimed, Inc., Maple Grove, MN (US)

(72) Inventor: Michael A. Knipfer, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/344,705

(22) Filed: Nov. 7, 2016

(65) Prior Publication Data

US 2017/0049547 A1   Feb. 23, 2017

Related U.S. Application Data

(63) Continuation of application No. 13/435,057, filed on Mar. 30, 2012, now Pat. No. 9,492,259.

(60) Provisional application No. 61/469,512, filed on Mar. 30, 2011.

(51) Int. Cl.
| | | |
|---|---|---|
| *A61F 2/00* | (2006.01) | |
| *A61B 17/34* | (2006.01) | |
| *A61B 17/00* | (2006.01) | |
| *A61B 17/04* | (2006.01) | |

(52) U.S. Cl.
CPC ........ *A61F 2/0045* (2013.01); *A61B 17/3468* (2013.01); *A61F 2/0009* (2013.01); *A61B 2017/00805* (2013.01); *A61B 2017/0412* (2013.01); *A61B 2017/0437* (2013.01); *A61F 2002/0068* (2013.01); *A61F 2002/0072* (2013.01); *A61F 2210/0004* (2013.01); *A61F 2210/0014* (2013.01); *A61F 2220/0016* (2013.01); *A61F 2250/0018* (2013.01); *A61F 2250/0031* (2013.01)

(58) Field of Classification Search
CPC ...... A61B 17/3468; A61B 2017/00805; A61B 2017/0437; A61F 2/0045; A61F 2002/0072; A61F 2220/0016; A61F 2210/0014; A61F 2250/0018; A61F 2250/0031; A61F 2002/0068; A61F 2210/0004
USPC ........................ 600/29, 30, 37; 128/897–899
See application file for complete search history.

(56) References Cited

U.S. PATENT DOCUMENTS

| | | |
|---|---|---|
| 6,612,977 B2 | 9/2003 | Staskin et al. |
| 6,648,921 B2 | 11/2003 | Anderson et al. |
| 6,691,711 B2 | 2/2004 | Raz et al. |
| 7,025,063 B2 | 4/2006 | Snitkin et al. |
| 7,070,556 B2 * | 7/2006 | Anderson .......... A61B 17/0401 112/169 |
| 7,303,525 B2 | 12/2007 | Watschke et al. |
| 7,347,812 B2 | 3/2008 | Mellier |
| 7,351,197 B2 | 4/2008 | Montpetit et al. |

(Continued)

FOREIGN PATENT DOCUMENTS

| | | |
|---|---|---|
| WO | 2007097994 A2 | 8/2007 |
| WO | 2008057261 A2 | 5/2008 |

*Primary Examiner* — Navin Natnithithadha
*Assistant Examiner* — Sunita Reddy
(74) *Attorney, Agent, or Firm* — Brake Hughes Bellermann LLP

(57) ABSTRACT

Various embodiments of a sling implant system are provided. Embodiments of the implants can include one or more collapsibility and expandability features or portions adapted to improve introduction and deployment of the implant within the patient. The implants can be folded, collapsed or otherwise reduced in size or construct to fit within a delivery tool or catheter for later expandability upon deployment of the implant.

22 Claims, 9 Drawing Sheets

(56) References Cited

U.S. PATENT DOCUMENTS

| | | |
|---|---|---|
| 7,407,480 B2 | 8/2008 | Staskin et al. |
| 7,500,945 B2 | 3/2009 | Cox et al. |
| 2002/0147382 A1 | 10/2002 | Neisz et al. |
| 2002/0151762 A1 | 10/2002 | Rocheleau et al. |
| 2004/0106847 A1* | 6/2004 | Benderev ........... A61B 17/0401 600/37 |
| 2008/0269547 A1* | 10/2008 | Hortenstine .......... A61F 2/0045 600/30 |
| 2008/0269548 A1* | 10/2008 | Vecchiotti ............ A61F 2/0045 600/30 |
| 2009/0156891 A1* | 6/2009 | Heys .................... A61F 2/0045 600/37 |
| 2009/0259092 A1* | 10/2009 | Ogdahl ................ A61F 2/0045 600/30 |
| 2010/0105979 A1 | 4/2010 | Hamel et al. |
| 2010/0198002 A1* | 8/2010 | O'Donnell ............ A61F 2/0045 600/30 |
| 2010/0261955 A1* | 10/2010 | O'Hern .............. A61B 17/0401 600/37 |
| 2010/0261956 A1* | 10/2010 | Townsend ............. A61F 2/0045 600/37 |
| 2010/0280309 A1* | 11/2010 | von Pechmann ........................... A61B 17/00234 600/37 |
| 2011/0174313 A1* | 7/2011 | von Pechmann ........................... A61B 17/00234 128/834 |
| 2011/0313241 A1* | 12/2011 | Benderev ........... A61B 17/0401 600/37 |
| 2012/0065649 A1* | 3/2012 | Towler ................. A61F 2/0045 606/151 |

* cited by examiner

EXPANDABLE IMPLANT SYSTEM

PRIORITY

This Application is a continuation of U.S. patent application Ser. No. 13/435,057, filed Mar. 30, 2012, which claims priority to and the benefit of U.S. Provisional Patent Application No. 61/469,512, filed Mar. 30, 2011; with each of the identified applications and disclosures full incorporated herein by reference.

FIELD OF THE INVENTION

The present invention relates generally to surgical methods and apparatus and, more specifically, to a surgically implantable sling adapted for selective collapsibility and expandability.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic mesh slings or implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include features adapted to provide selective expandability and collapsibility of the implant.

The implant has an expanding member associated with the support portion. The expanding member maintains a collapsed state until deployed into the anchoring tissue. The implant can thereby be inserted utilizing a smaller incision and no dissecting. Once at the target tissue, the implant is released and the expansion member expands to its expanded state. The expanded state provides a bulking area near the urethra and aids in preventing migration.

Embodiments of the present invention may be incorporated into or provided with various commercial products marketed by American Medical Systems of Minnetonka, Minn., as the MiniArc® Single-Incision Sling and like implant or anchoring systems.

DETAILED DESCRIPTION OF PREFERRED EMBODIMENTS

Figures 1A, 1B:
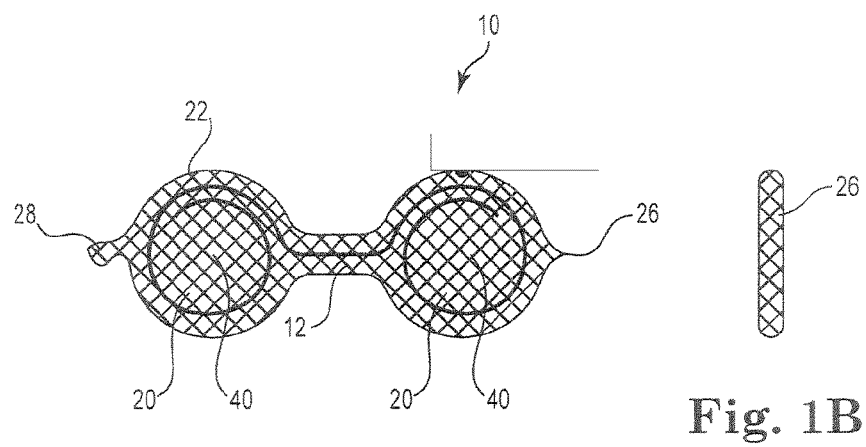
FIG. 1A is a perspective view of an embodiment of the implant according to an aspect of the present invention.
FIG. 1B is a perspective view of FIG. 1A.

The following description is meant to be illustrative only and not limiting. Other embodiments of this invention will be apparent to those of ordinary skill in the art in view of this description. The present invention is particularly suitable for treating stress urinary incontinence (SUI) diagnosed with urethral hypermobility or intrinsic sphincter deficiency in both men and women. Although the invention as disclosed herein generally refers to SUI, treatment of other urological disorders, such as urge incontinence, mixed incontinence, overflow incontinence, functional incontinence, prolapse (e.g. vaginal), enteroceles (e.g. of the uterus), rectoceles and other non-urological disorders, are also included within the scope of the present invention. It is contemplated that the present invention may also be utilized in conjunction with other procedures, such as, but not limited to, procedures for addressing cystocele prolapse, vaginal prolapse and anatomic hypermobility.

In general, the implant systems 10 can include an implant and a delivery device. The implant can include a support portion 12, and end portions 26 having anchors 16 provided therewith. Various portions of the implant systems 10 can be constructed of polymer materials, such as a film or sheet material of polypropylene, polyethylene, fluoropolymers or like compatible materials.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0105979, 2002/151762 and 2002/147382. Accordingly, the above-identified disclosures are fully incorporated herein by reference in their entirety.

Figure 2A:
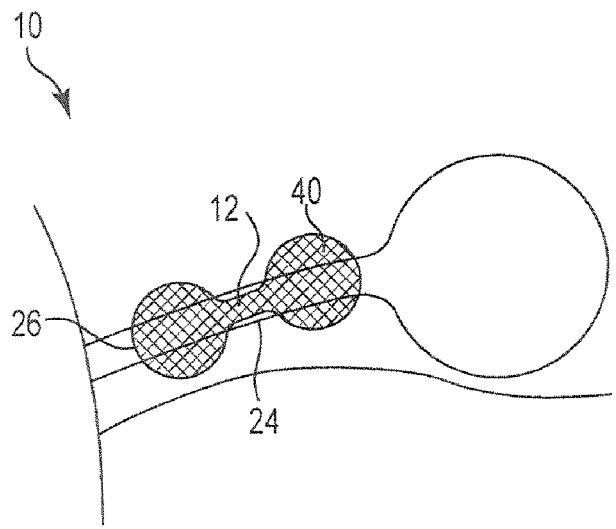
FIG. 2A is a schematic view of the implant of FIG. 1A in vitro.
Figure 2B:
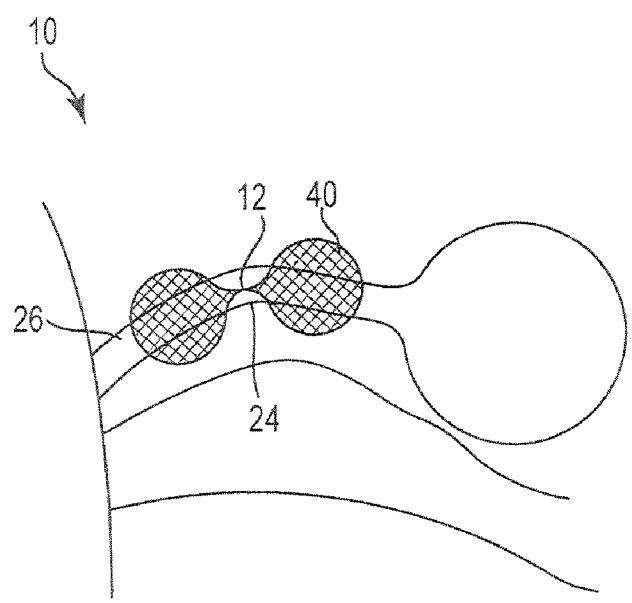
FIG. 2B is a lateral schematic view of the implant of FIG. 1A in vitro in a flexed state.
Figure 3A:
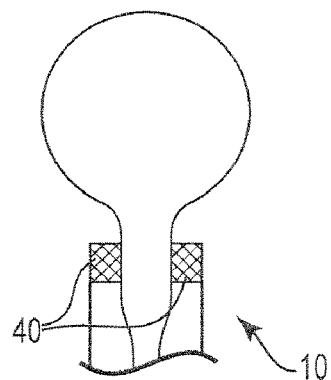
FIG. 3A is a perspective schematic view of the implant of FIG. 1A in vitro.
Figure 3B:
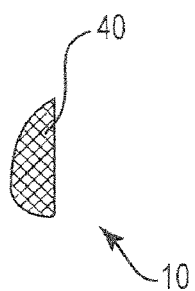
FIG. 3B is a lateral view of FIG. 3A.
Figure 3C:
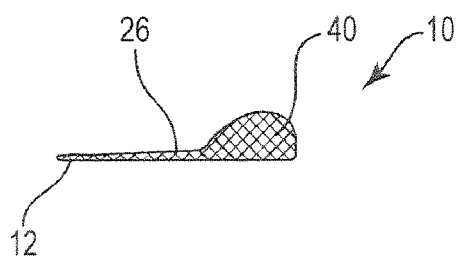
FIG. 3C is a superior view of FIG. 3A.

Referring generally to FIGS. 1-3, an embodiment of the implant systems 10 can be constructed of a mesh polymer 22 hybrid and a nitinol coil 20 or like material construct that collapses into a needle for deployment and delivery. The expanding design eliminates or reduces the need for dissection during implantation. The shape and configuration of the implant systems 10 will resist migration forces lateral to or with respect to the urethra, thereby maintaining the treatment location of a bulking feature proximate to a sphincter of a patient. In various embodiments, the implant system 10 is delivered percutaneously.

As shown in FIGS. 1A & 1B, an example embodiment of implant systems 10 has a support portion 12 and one or more end portions 26. The support portion 12 may also include a Nitinol or like coil or expanding member 40 that can be included within or with a mesh tube 22. Various attributes, sizes, shapes and like characteristics can be provided for the implant systems 10 and mesh tube 22. In various embodiments, the implant system 10 defines a generally figure-eight structure with a hinge point at the support portion 12 and two end portions 26. A segment of the support portion 12 may be narrower in size than the end portion 26.

As shown in FIG. 2, the implant system 10 may be deployed proximal to the urethra and capable of expanding to provide a desired level of force against the urethra. In one embodiment, the support portion 12 or a portion thereof may flex to provide movement with the urethra.

FIG. 3 demonstrates an alternative embodiment of the implant systems 10. The implant system 10 may include a support portion 12 and one or more end portions 26. An expansion member 40 may be coupled to support portion 12 to provide a bulking mechanism positioned proximal to a sphincter.

Figure 4:
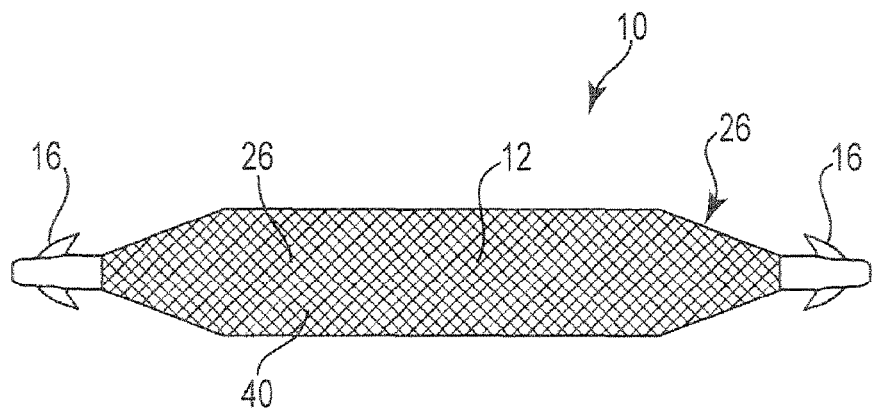
FIG. 4 is an embodiment of the implant of the present invention.

Other embodiments of the implant systems 10 can include a mesh design and 20 configuration adapted to provide folding or collapsibility to facilitate insertion and deployment of the implant within the patient. As shown in FIGS. 4-11, various collapsibility and expansion features 40 can be included with the implant. FIG. 4 shows an embodiment of implant system 10. Implant system 10 has a support portion 12 and end portion 28. End portion 26 may be coupled to a fixation device 16. Fixation device 16 may be a soft tissue anchor, suture, or other similar structure. Implant system 10 may be constructed of a collapsible mesh material to facilitate compression within an insertion device.

FIG. 4 shows an alternative embodiment of implant system 10. Implant system 10 has a support portion 12 and end portion 26. End portion 26 may be coupled to a fixation device 16 such as a soft tissue anchor or suture. The implant system 10 may be configured to fold or collapse to facilitate deployment and implantation within the patient.

As depicted in FIG. 4-7, an alternative embodiment of the implant systems 10 can include a widened portions or segments of the support portion 12 (FIGS. 5, 10), narrowing segment of the support portion 12 (FIGS. 6-7, 11), or other ribbed, folded or otherwise defined support portion 12 segments (FIG. 8) to facilitate collapsibility and expansion upon deployment. Various embodiments can include a biodegradable or absorbable sections to promote the described expansion of the implant features.

Figure 5:
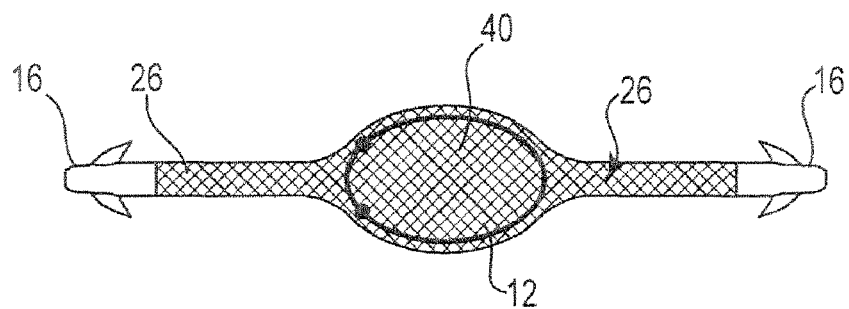
FIG. 5 is another embodiment of the present invention.

FIG. 5 illustrates another embodiment of implant system 10. Implant system 10 has support portion 12 and one or more end portions 26 coupled to a fixation device 16. Fixation device 16 may be a soft tissue anchor, suture, or other anchoring mechanism. The support portion 12 or portions thereof may be narrower than the end portions 26 to aid in insertion into and deployment out of a flat needle. Implant 10 may be comprised of a mesh or other similar material that can collapse or fold into an insertion tool 32.

Figure 6:
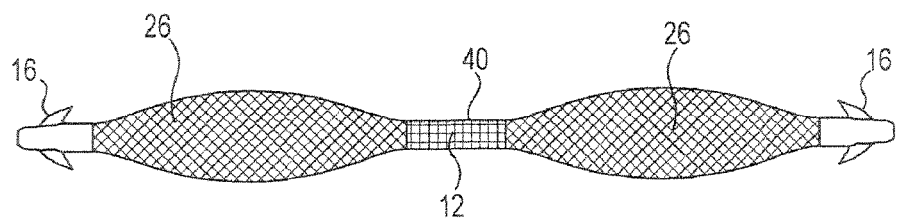
FIG. 6 is another embodiment of the present invention.

In yet another embodiment, the implant system 10 of FIG. 6 is comprised of support portion 12 coupled to one or more end portions 26. End portions 26 may be coupled to a fixation device 16 such as a soft tissue anchor or other like mechanism. Implant system 10 may be comprised of a mesh or other similar material that can collapse or fold into an insertion tool 32. End portions 26 and/or expansion member 40 may be comprised of a tubular mesh that may expand upon deployment. Support portion 12 may be comprised of an absorbable or non-absorbable material.

Figure 7:
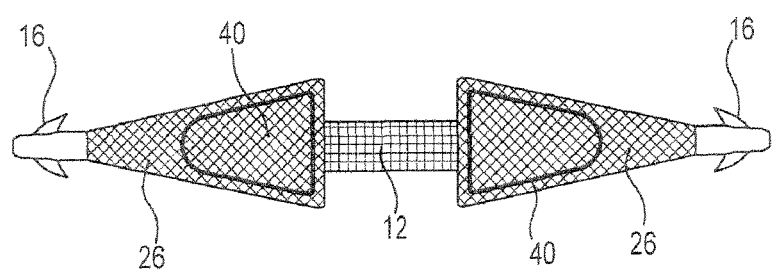
FIG. 7 is another embodiment of the present invention.

FIG. 7 illustrates an implant system 10 where a segment of the support portion 12 is less than the width of the expansion portions 40. The support portion 12 and associated end portions 26 may be composed of absorbable, non-absorbable mesh or a combination. Support portion 12 and expansion member 40 may be narrower than end portions 26 before deployment and widen once placed in the patient. End portions 26 may be operatively coupled to a fixation device 16 capable of anchoring within a target tissue.

Figure 8A:
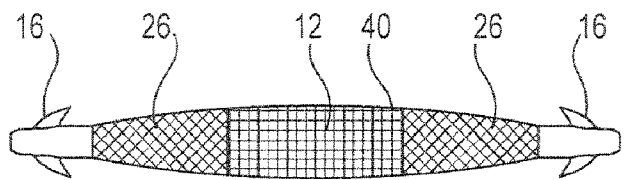
FIG. 8A is a collapsed view of another embodiment of the present invention.
Figure 8B:
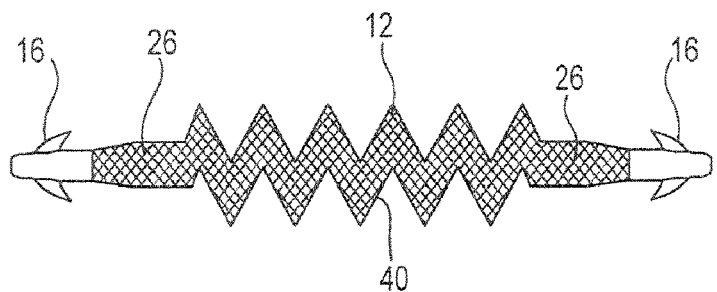
FIG. 8B is a side view of the implant of FIG. 8A in an expanded state.
Figure 8C:
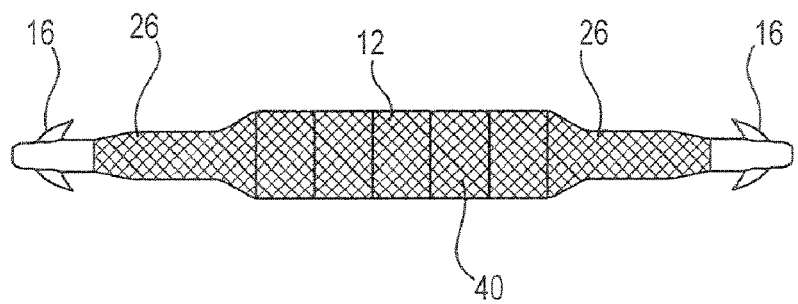
FIG. 8C is a perspective view of FIG. 8B.

FIGS. 8A-C show an implant system 10 that may fold into a flat needle. Support portion 12 and end portions 26 may be made from mesh or a similar material. Support portion 12 may fold, i.e., like an accordion to fit in a needle, ideally 4 mm in width. The implant would be compressed to fit into the flat needle and upon deployment support portion 12, end portion 26, and/or expansion feature 40 would unfold to provide a wider implant section proximal to the urethra.

Figure 9:
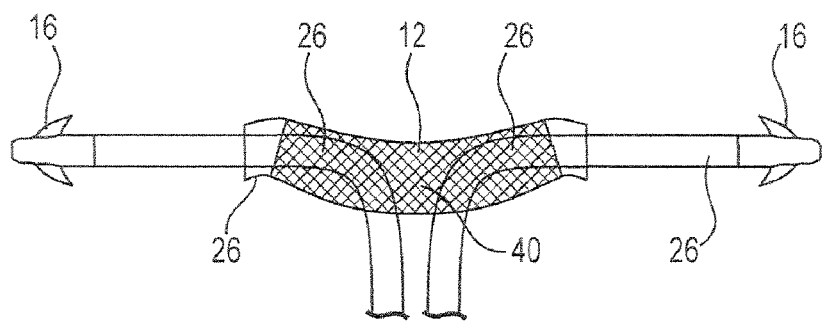
FIG. 9 is another embodiment of the present invention.
Figure 10:
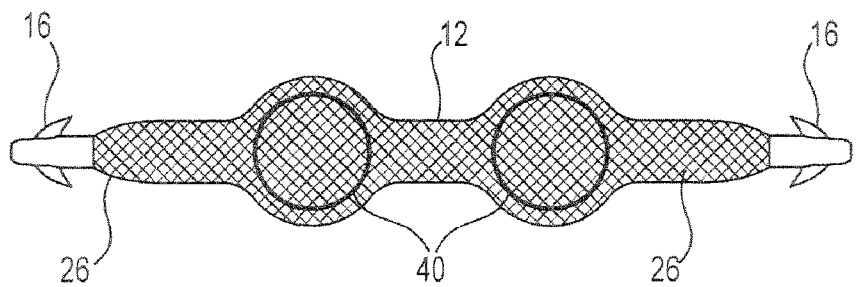
FIG. 10 is another embodiment of the present invention.
Figure 11:
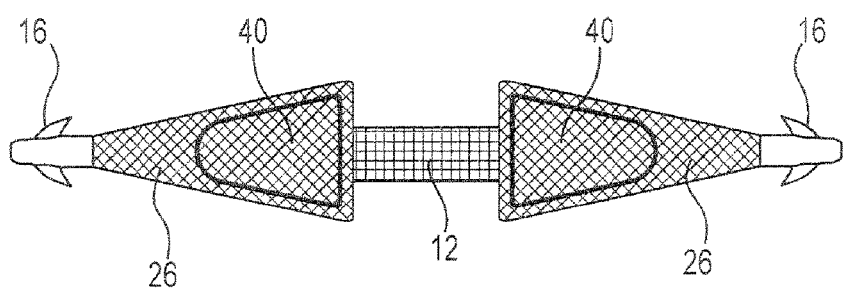
FIG. 11 is yet another embodiment of the present invention.

FIGS. 9-11 show various alternative embodiments of the collapsible and expandable implant system 10. Each can be folded, collapsed or otherwise provided within or with a delivery tool for deployment. FIG. 9 shows an embodiment wherein the mesh slides along a suture placed in the target tissue. The suture may be woven within the end portions 26. The implant system 10 of FIG. 10 may include one or more expansion elements 40 in the form of tubular mesh. The expansion elements 40 may be circular or ovular is shape. It will be obvious to one skilled in the art that other shapes and configurations may be employed without departing from the spirit and scope of the invention. The expansion elements 40 are adapted to fit within and deploy from the needle 34 of the delivery tool 32. FIG. 11 depicts an alternative embodiment of the implant system 10 wherein a segment of the support portion 12 may include an absorbable or non-absorbable material or containing an absorbable coating. The expansion members 40 would be adapted to fit within the needle or catheter device.

Figure 12A:
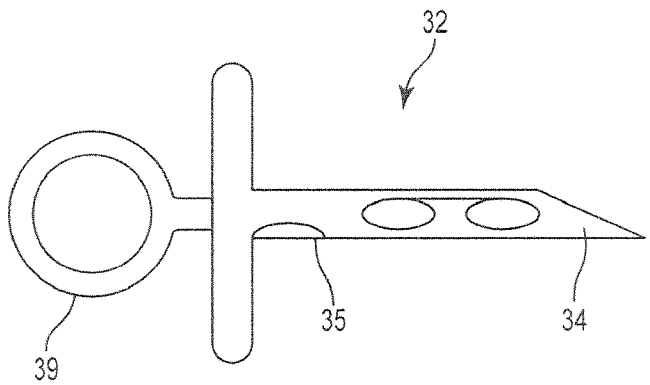
FIG. 12A is an illustration of an embodiment of an insertion device.
Figure 12B:
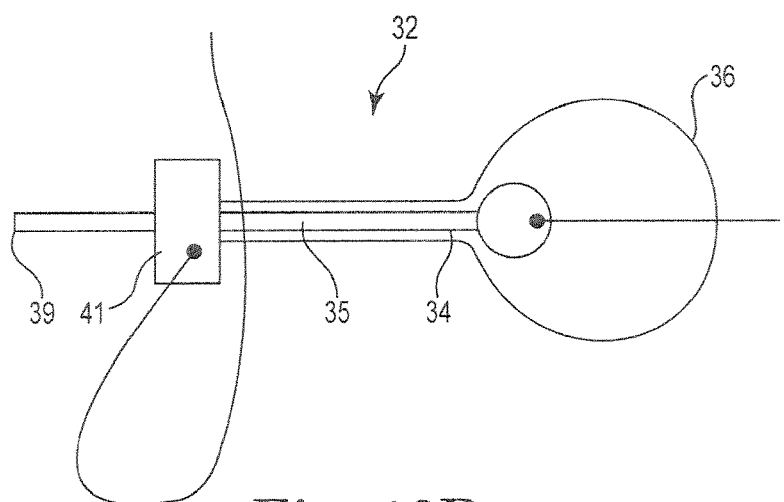
FIG. 12B is another embodiment of an insertion device.
Figure 13:
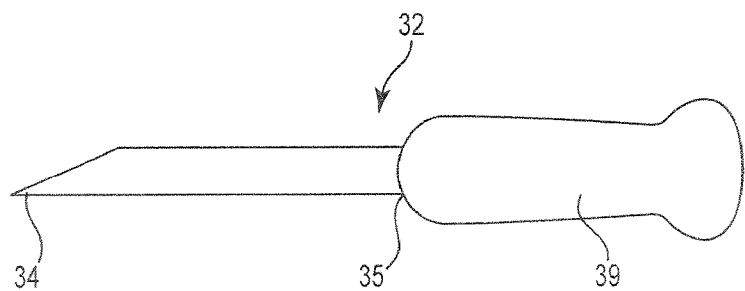
FIG. 13 is another embodiment of an insertion device.

An embodiment of a delivery tool 32 is shown in FIG. 12A & B. The delivery tool 32 comprises a needle 34 coupled to the distal end of a handle 39. The needle 34 would allow for the implant to be loaded therein. An alternative insertion tool 32 embodiment is illustrated in FIG. 12B. Insertion tool 32 may have indicia 41 located on handle 39 to aid in implantation. Additionally, a shaft 35 may include a catheter 36 with a balloon located on the distal end. The insertion tool 32 and its respective components are designed to provide selective insertion, ejection and expansion of the implant system 10 within the patient for deployment at the patient's urethra. FIG. 12B illustrates associated implantation tool 32. Insertion tool 32 has a handle 39 on proximal end and a needle 34 on the distal end. The needle 34 may embody a substantially flat shape. Support portion 12 and expansion member 40 can be folded to fit into the needle 34.

In general, the support portion 12 can be configured to fit within a 0.090" ID delivery tool, for deployment from the tool. Other support portions 12 can fit into a 4 mm wide delivery tool. Other various implant and tool designs and shapes can be used as well. With such an implant and tool system, the need for an incision and lateral dissection is eliminated, because the implant can be delivered and deployment from within the tool. As such, tissue disruption and bleeding is reduced.

The implant systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant to treat a pelvic disorder, comprising:
   a mesh constructed at least in part of a plurality of interwoven filaments,
   the mesh including a support portion configured to engage a portion of a urethra of a patient, the mesh includes a first end portion and a second end portion defining a longitudinal line, the support portion being disposed between the first end portion and the second end portion, the support portion including a first expandable member disposed within the support portion at a first location, a second expandable member disposed within the support portion at a second location, and a central region disposed between the first location and the second location, the first expandable member being configured to expand in a transverse direction with respect to the longitudinal line, wherein a first portion of the support portion is configured to expand to a size larger than a size of the central region during an expanded state of the first expandable member.

2. The implant of claim 1, wherein the first expandable member is adjustable between a collapsed state and the expanded state, the first portion of the support portion having a generally circular shape in response to the first expandable member being within the expanded state.

3. The implant of claim 1, further comprising:
   a fixation device coupled to the first end portion of the implant.

4. The implant of claim 3, wherein the fixation device includes a suture.

5. The implant of claim 3, wherein the fixation device includes a soft tissue anchor.

6. The implant of claim 1, wherein the support portion includes an absorbable material.

7. The implant of claim 1, wherein the support portion is configured to be inserted into a needle of a delivery tool.

8. The implant of claim 1, wherein the first portion of the support portion defines a bulking area positionable near the urethra to operatively engage the portion of the urethra in response to the first expandable member being within the expanded state.

9. The implant of claim 1, wherein the second expandable member is configured to expand a second portion of the support portion to a size larger than the size of the central region.

10. The implant of claim 1, further including a suture coupled to a first end portion of the mesh.

11. The implant of claim 1, wherein the first expandable member includes a first nitinol coil portion, and the second expandable member includes a second nitinol coil portion.

12. The implant of claim 11, wherein the first nitinol coil portion and the second nitinol coil portion are defined by a nitinol wire member, the nitinol wire member having a portion extending across the central region that connects the first nitinol coil portion and the second nitinol coil portion, the portion extending across the central region being devoid of a coil.

13. The implant of claim 1, further comprising:
   a first anchor coupled to the first end portion; and
   a second anchor coupled to the second end portion.

14. The implant of claim 1, wherein the first expandable member is unitarily constructed with the support portion.

15. The implant of claim 1, wherein the second expandable member is unitarily constructed with the support portion.

16. A method of treating a pelvic disorder in a patient, comprising:
   creating an incision;
   providing an insertion tool;
   providing an implantable sling having a mesh support portion, the mesh support portion having at least one expandable member, the mesh support portion includes a first end portion and a second end portion defining a longitudinal line, the implantable sling defining a generally tubular shape that is adjustable between a collapsed state and an expanded state;
   coupling the implantable sling in the collapsed state to a delivery tool;
   inserting, via the incision, the implantable sling in the collapsed state into a body of the patient using the delivery tool;
   releasing the implantable sling from the delivery tool at or near a urethra of the patient to provide the at least one expandable member to expand in a transverse direction with respect to the longitudinal line and place the implantable sling in the expanded state; and removing the insertion tool via the incision, leaving the implantable sling in place.

17. The method of claim 16, wherein the at least one expandable member includes a first expandable member disposed within the implantable sling at a first location, and a second expandable member disposed within the implantable sling at a second location.

18. The method of claim 16, wherein the coupling includes inserting the mesh support portion into a needle of the delivery tool.

19. The method of claim 16, wherein the implantable sling includes a first end portion, and a second end portion, the mesh support portion being disposed between the first end portion and the second end portion, the implantable sling including a fixation device coupled to the first end portion, the method further comprising:

anchoring the fixation device to target tissue within the body of the patient.

20. The method of claim 16, wherein the implantable sling in the expanded state provides a bulking area near the urethra to aid in preventing migration of the urethra.

21. An implant to treat a pelvic disorder, comprising:

a sling having a support portion defined by a mesh tube, the mesh tube includes a first end portion and a second end portion defining a longitudinal line, the support portion configured to engage a portion of a urethra of a patient, the support portion including at least one expandable member disposed within the mesh tube, the at least one expandable member configured to be within a collapsed state after being coupled to a delivery tool, the at least one expandable member configured to transition to an expanded state after being released from the delivery tool, the at least one expandable member being configured to expand in a transverse direction with respect to the longitudinal line, wherein a portion of the support portion is configured to expand to a size larger than a size of the mesh tube during the expanded state of the at least one expandable member and the portion of the mesh tube defining a bulking area positionable near the urethra to operatively engage the portion of the urethra.

22. The implant of claim 21, wherein the at least one expandable member is unitarily constructed with the support portion.

* * * * *